United States Patent
Wood et al.

(12) 
(10) Patent No.: US 6,358,883 B1
(45) Date of Patent: Mar. 19, 2002

(54) PESTICIDAL AND PARASITICIDAL USE OF 1-ARYL-1-(SUBSTITUTED THIO, SULFINYL AND SULFONYL)-2-NITROETHANE COMPOUNDS

(75) Inventors: William Wakefield Wood, Pennington; Annmarie Enos, Cranbury, both of NJ (US)

(73) Assignee: American Cyanamid Company, Madison, NJ (US)

( * ) Notice: Subject to any disclaimer, the term of this patent is extended or adjusted under 35 U.S.C. 154(b) by 0 days.

(21) Appl. No.: 09/434,361

(22) Filed: Nov. 5, 1999

Related U.S. Application Data
(60) Provisional application No. 60/108,582, filed on Nov. 16, 1998.

(51) Int. Cl.$^7$ ...................... A01N 43/10; C07D 333/12; C07D 307/02; C07D 315/00; C07D 205/00
(52) U.S. Cl. ...................... 504/130; 504/140; 504/289; 504/294; 504/350; 504/355; 549/75; 549/492; 568/30; 568/927
(58) Field of Search ................................ 504/130, 140, 504/289, 294, 350, 355; 549/75, 492; 568/30, 927

(56) References Cited

U.S. PATENT DOCUMENTS
3,882,247 A  5/1975  Bullock ...................... 424/337

FOREIGN PATENT DOCUMENTS
JP    57175190   * 10/1982
JP    62039563     2/1987  ......... C07C/145/00

OTHER PUBLICATIONS
CA 127:5048, Basel, 1997.*
CA 121:8293, Kim, 1994.*
CA 118:168778, Fuji, 1992.*
CA 113:152312, Hassner, 1990.*
CA 84:59982, Jung, 1975.*
C. Bernasconi et al. Journal of Organic Chemistry, 57, pp. 2365–2373 (1992).
N. Kobayashi et al. Journal of Organic Chemistry, 46, pp. 1823–1828 (1981).
C. Bernasconi et al. Journal of the American Chemical Society, 111, pp. 6862–6864 (1989).
R. Jabobo et al. Journal of Flourine Chemistry, 67, pp. 253–255 (1994).
A. Jara et al., Synthetic Communications, 24(3), pp. 417–426 (1994).
B. Baker et al., Journal of Organic Chemistry, 12, pp. 138–154 (1947).
Nagao, Y. et al. "A new carbon bond formation at the beta position of 3,4–dimethoxy–E–beta–nitrostyrene" Tetrahed. Lett. vol. 15, pp. 1215–1218, 1976.
Dehaen, W. et al. "Stereoselectivity in intramolecular 1,3–dipolar cycloadditions. Nitrile oxides versus silyl nitronates" Tetrahed. Lett. vol. 31, pp. 743–746, 1990.
Kim, J. et al. "A Convenient Synthesis Of Isothiocy Anates From Primary Nitroalkanes", Synthetic Communications, 24(8), 1101–1105 (1994) pp. 1101–1105.
Fuji, K. et al. "Hard Acid and Soft Nucleophile Systems. Part 14. On the Reactivity of α–Nitroketones and Nitroolefins Toward a Aluminum Chloride and Ethanethiol System", Bull. Inst. Chem. Res. Kyoto Univ. vol. 70, No. 3, 1992, pp. 318–325.
Hassner A. et al. "A Two–Step Conversion of Carbonyl Compounds into Functionalized Five– and Six–Membered Ring Thioethers via Intramolecular Cycloaddition", J. Org. Chem. 1990, 55, pp. 5505–5510.
Basel, Y. et al. "An Improved Method for Preparation of Nitrile Oxides from Nitroalkanes for In Situ Dipolar Cycloadditions", Synthesis, Mar. 1997, pp. 309–312.
H. R. Hyoung, et al. "Double diastereoselectivity in the intramolecular nitrile oxide–olefin cycloaddition (INOC) reaction" Tetrahedron Letters, vol. 32, No. 34, 1991, pp. 4259–4262.
T.–R. Kim et al, "Synthesis of nucleophilic adducts of thiols (I). Addition of cysteine to beta–nitrostyrene derivatives", Bulletin of Korean Chemical Society, vol. 2, No. 4, 1981, pp. 125–129.
E. Sturdik et al. "Reaction of vinylfurans with sulfhydryl and amino groups", Biochemical Pharmacology vol. 28, No. 16, 1979, pp. 2525–2530.
W. Winter, et al. "X–ray structure analysis, absolute configuration, and adducts of cysteine", Chemische Berichte, vol. 112, No. 7, 1979, pp. 3171–3189 (English language Abstract).
M. Rosenberg, et al. "Reactivity of 2–furylethylenes with nucleophylic groups and its biological significance" Collection of Czechoslovak Chemical Communications, vol. 52, No. 2, 1987, pp. 425–430.
R. L. Heath et al. "Aliphatic nitro–compounds. Part IV. Addition of thiols to alpha–nitro–olefins" Journal of The Chemical Society, 1947, pp. 1477–1481.
S. Balaz, et al. "Biochemically important reactions of 2–furylethylenes. Characterization of the reactivity towards thiols" Collection of Czechoslovak Chemical Communications, vol. 47, No. 6, 1982, pp. 1659–1666.

* cited by examiner

*Primary Examiner*—D. Margaret Seaman
(74) *Attorney, Agent, or Firm*—Charles F. Costello

(57) ABSTRACT

The present invention relates to the pesticidal use of 1-aryl-1-(substituted thio, sulfinyl and sulfonyl)-2-nitroethane compounds having the structural formula I

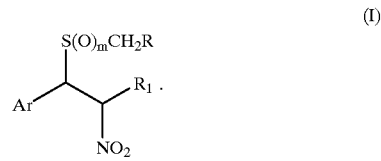

15 Claims, No Drawings

PESTICIDAL AND PARASITICIDAL USE OF 1-ARYL-1-(SUBSTITUTED THIO, SULFINYL AND SULFONYL)-2-NITROETHANE COMPOUNDS

This application claims priority from copending provisional application(s) Ser. No. 60/108,582 filed on Nov. 16, 1998.

BACKGROUND OF THE INVENTION

Nematode, insect and acarid pests destroy growing and harvested crops. In the United States, agronomic crops must compete with thousands of those pests. In addition, helminth parasites cause hundreds of millions of dollars in economic damage to the livestock and companion animal sectors annually on a global basis.

In spite of the commercial pesticides and parasiticides available today, damage to crops, livestock, companion animals and humans still occurs. Accordingly, there is ongoing research to create new and more effective pesticides and parasiticides.

Certain β-nitrophenethyl derivatives which are useful as fungicidal agents are described in JP 62039563. However, that application does not describe or suggest any nematicidal, insecticidal and acaricidal utility for the β-nitrophenethyl derivatives described therein.

It is, therefore, an object of the present invention to provide a method for the control of helminth, nematode, insect and acarid pests and parasites.

It is also an object of the present invention to provide a method for the protection of growing and harvested crops from damage caused by nematode, insect and acarid attack and infestation.

It is a further object of this invention to provide a method for treating, controlling, preventing and protecting warm-blooded animals, fish and humans against infestation and infection by helminths These and other objects of the present invention will become more apparent from the description thereof set forth below.

SUMMARY OF THE INVENTION

The present invention provides a method for the control of helminth, nematode, insect or acarid pests or parasites which comprises contacting said pests or parasites or their food supply, habitat or breeding grounds with a pesticidally or parasiticidally effective amount of a 1-aryl-1-(substituted thio, sulfinyl or sulfonyl)-2-nitroethane compound having the structural formula I

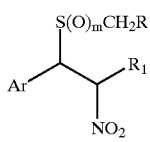

(I)

wherein
Ar is phenyl optionally substituted with any combination of one to five halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups, one to three $C_1$–$C_4$halo-alkylthio groups, one benzylthio group or one $SCH_2CO_2R_2$ group, 1- or 2-naphthyl optionally substituted with any combination of one to five halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups, piperonyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups, 2-, 3- or 4-pyridyl optionally substituted with any combination of one to four halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups, 2- or 3-furyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups, or 2- or 3-thienyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups;

R is hydrogen, $CO_2R_3$, $C(O)NR_4R_5$, $(CH_2)_nCR_2(NR_4R_5)$ $CO_2R_3$, $CH(OR_6)CH_2OR_7$, $CH(CH_2OR_8)SCH(R_9)$ $CH_2NO_2$, $C_1$–$C_4$alkyl, $C_1$–$C_4$haloalkyl, $C_2$–$C_4$alkenyl, $C_2$–$C_4$haloalkenyl, phenyl optionally substituted with any combination of one to five halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups, 2- or 3-furyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups, or 2- or 3-thienyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups;

$R_2$, $R_6$, $R_7$ and $R_8$ are each independently hydrogen or $C_1$–$C_6$alkyl;

m is 0, 1 or 2;

n is 0 or 1;

$R_9$ is phenyl optionally substituted with any combination of one to five halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$halo-alkylthio groups;

$R_3$ is hydrogen, $C_1$–$C_{10}$alkyl, $CH_2(C_1$–$C_{10}$haloalkyl), $C_3$–$C_{10}$alkenyl, $C_3$–$C_{10}$haloalkenyl, a cation, benzyl optionally substituted on the ring with any combination of one to five halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups, or phenyl optionally substituted with any combination of one to five halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups;

$R_4$ and $R_5$ are each independently hydrogen, $C_1$–$C_{10}$alkyl, $CH_2$ ($C_1$–$C_{10}$haloalkyl), $C_3$–$C_{10}$alkenyl, $C_3$–$C$haloalkenyl, benzyl optionally substituted on the ring with any combination of one to five halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups, or phenyl optionally substituted with any combination of one to five halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups, and when $R_4$ and $R_5$ are taken together with the atom to which they are attached, they may form a five- or six-membered ring wherein $R_4R_5$ is represented by: —$(CH_2)_4$—, —$(CH_2)_5$— or —$(CH_2)_2O(CH_2)_2$—; and $R_1$ is hydrogen, $C_1$–$C_4$alkyl or phenyl optionally substituted with any combination of one to five halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups.

This invention also comprises pesticidal and parasiticidal compositions containing those compounds. Advantageously, it has been found that the 1-aryl-1-(substituted thio, sulfinyl and sulfonyl)-2-nitroethane compounds, and compositions containing them, are especially useful for the control of nematode pests.

DETAILED DESCRIPTION OF THE INVENTION

The present invention provides a method for the control of helminth, nematode, insect or acarid pests or parasites which comprises contacting said pests or parasites their food supply, habitat or breeding grounds with a pesticidally or parasiticidally effective amount of a 1-aryl-1-(substituted thio, sulfinyl or sulfonyl)-2-nitroethane compound of formula I.

Preferred formula I pesticidal agents of this invention include methyl{[alpha-(nitromethyl)benzyl]thio}acetate;
{[alpha-(nitromethyl)benzyl]thio}acetic acid;
ethyl{[p-methyl-alpha-(nitromethyl)benzyl]thio}acetate;
butyl{[alpha-(nitromethyl)benzyl]thio}acetate;
methyl{[3,4-(methylenedioxy)-alpha-(nitromethyl)benzyl]thio}acetate;
ethyl{[3,4-(methylenedioxy)-alpha-(nitromethyl)benzyl]thio}acetate;
butyl{[3,4-(methylenedioxy)-alpha-(nitromethyl)benzyl]thio}acetate;
methyl{[p-methyl-alpha-(nitromethyl)benzyl]thio}acetate;
butyl{[p-methyl-alpha-(nitromethyl)benzyl]thio}acetate;
methyl{[o-fluoro-alpha-(nitromethyl)benzyl]thio}acetate;
ethyl{[o-fluoro-alpha-(nitromethyl)benzyl]thio}acetate;
butyl{[o-fluoro-alpha-(nitromethyl)benzyl]thio}acetate;
methyl{[p-methoxy-alpha-(nitromethyl)benzyl]thio}acetate;
ethyl{[p-methoxy-alpha-(nitromethyl)benzyl]thio}acetate;
butyl{[p-methoxy-alpha-(nitromethyl)benzyl]thio}acetate;
p-[1-(allylthio)-2-nitroethyl]anisole;
methyl{[m-methoxy-alpha-(nitromethyl)benzyl]thio}acetate;
ethyl{[m-methoxy-alpha-(nitromethyl)benzyl]thio}acetate;
{[p-fluoro-alpha-(nitromethyl)benzyl]thio}acetic acid;
{[3,4-(methylenedioxy)-alpha-(nitromethyl)benzyl]thio}acetic acid;
{[2-nitro-1-(p-tolyl)ethyl]thio}acetic acid;
{[p-isopropyl-alpha-(nitromethyl)benzyl]thio}acetic acid;
{[o-fluoro-alpha-(nitromethyl)benzyl]thio}acetic acid;
{[m-methoxy-alpha-(nitromethyl)benzyl]thio}acetic acid;
{[p-methoxy-alpha-(nitromethyl)benzyl]thio}acetic acid;
{[p-chloro-alpha-(nitromethyl)benzyl]thio}acetic acid;
2,3-bis{[alpha-(nitromethyl)benzyl]thio}-1-propanol;
3-{[alpha-(nitromethyl)benzyl]thio}alanine;
{[2-nitro-1-(2-thienyl)ethyl]thio}acetic acid;
ethyl{[2-nitro-1-(2-thienyl)ethyl]thio}acetate;
2-[1-(allylthio)-2-nitroethyl]thiophene; and
3-[1-(allylthio)-2-nitroethyl]pyridine, among others.

More preferred pesticidal agents of this invention which are especially useful for the control of nematodes include methyl{[alpha-(nitromethyl)benzyl]thio}acetate;
{[alpha-(nitromethyl)benzyl]thio}acetic acid;
ethyl{[p-methyl-alpha-(nitromethyl)benzyl]thio}acetate;
ethyl{[3,4-(methylenedioxy)-alpha-(nitromethyl)benzyl]thio}acetate;
methyl{[p-methyl-alpha-(nitromethyl)benzyl]thio}acetate;
ethyl{[p-methoxy-alpha-(nitromethyl)benzyl]thio}acetate;
{[p-fluoro-alpha-(nitromethyl)benzyl]thio}acetic acid;
{[3,4-(methylenedioxy)-alpha-(nitromethyl)benzyl]thio}acetic acid;
{[2-nitro-1-(p-tolyl)ethyl]thio}acetic acid;

{[p-isopropyl-alpha-(nitromethyl)benzyl]thio}acetic acid;
{[o-fluoro-alpha-(nitromethyl)benzyl]thio}acetic acid;
{[m-methoxy-alpha-(nitromethyl)benzyl]thio}acetic acid;
{[p-methoxy-alpha-(nitromethyl)benzyl]thio}acetic acid;
2,3-bis{[alpha-(nitromethyl)benzyl]thio}-1-propanol; and
3-{[alpha-(nitromethyl)benzyl]thio}alanine, among others.

The present invention also provides a method for the protection of growing plants from attack or infestation by nematode, insect or acarid pests which comprises applying to the foliage of the plants, or to the soil or water in which they are growing, a pesticidally effective amount of a 1-aryl-1-(substituted thio, sulfinyl or sulfonyl)-2-nitroethane compound of formula I.

The formula I compounds of this invention are useful for the control of plant parasitic nematodes and nematodes living freely in soil. Plant parasitic nematodes include, but are not limited to, ectoparasites such as Xiphinema spp., Longidorus spp. and Trichodorus spp.; semi-parasites such as Tylenchulus spp.; migratory endoparasites such as Pratylenchus spp., Radopholus spp. and Scutellonema spp.; sedentary parasites such as Heterodera spp., Globodera spp. and Meloidogyne spp.; and stem and leaf endoparasites such as Ditylenchus spp., Aphelenchoides spp. and Hirshmaniella spp.

The 1-aryl-1-(substituted thio, sulfinyl and sulfonyl)-2-nitroethane compounds of formula I are also useful for controlling insect and/or acarid pests. Insects controlled by the formula I compounds of this invention include, but are not limited to, Lepidoptera such as tobacco budworms, cabbage loopers, cotton boll worms, beet armyworms, southern armyworms and diamondback moths; Homoptera such as aphids, leaf hoppers, plant hoppers and white flies; Thysanoptera such as thrips; Coleoptera such as boll weevils, Colorado potato beetles, southern corn rootworms, western corn rootworms and mustard beetles; and Orthoptera such as locusts, crickets, grasshoppers and cockroaches. Acarina controlled by the formula I compounds of this invention include, but are not limited to, mites such as two-spotted spider mites, carmine spider mites, banks grass mites, strawberry mites, citrus rust mites and leprosis mites.

In practice generally about 0.1 ppm to about 10,000 ppm and preferably about 1 ppm to about 5,000 ppm of a formula I compound, dispersed in water or another liquid carrier, is effective when applied to plants or the soil or water in which the plants are growing or are to be grown to protect the plants from nematode, insect and/or acarid attack and infestation.

The 1-aryl-1-(substituted thio, sulfinyl and sulfonyl)-2-nitroethane compounds are also effective for controlling nematode, insect and/or acarid pests when applied to the foliage of plants and/or to the soil or water in which said plants are growing or are to be grown in sufficient amount to provide a rate of about 0.1 kg/ha to 4.0 kg/ha of active ingredient.

While the formula I compounds of this invention are effective for controlling nematode, insect and/or acarid pests of agronomic crops, both growing and harvested, when employed alone, they may also be used in combination with other biological agents used in agriculture, including, but no limited to, other nematicides, insecticides and/or acaricides. For example, the formula I compounds of this invention may be used effectively in conjunction or combination with pyrethroids, phosphates, carbamates, cyclodienes, endotoxin of *Bacillus thuringiensis* (Bt), formamidines, phenol tin compounds, chlorinated hydrocarbons, benzoylphenyl ureas, pyrroles and the like.

The compounds of this invention may be formulated as emulsifiable concentrates, flowable concentrates or wettable powders which are diluted with water or other suitable polar solvent, generally in situ, and then applied as a dilute spray. Said compounds may also be formulated in dry compacted granules, granular formulations, dusts, dust concentrates, suspension concentrates, microemulsions and the like all of which lend themselves to seed, soil, water and/or foliage applications to provide the requisite plant protection. Such formulations or compositions of the present invention include a formula I compound of this invention (or combinations thereof) admixed with one or more agronomically acceptable inert, solid or liquid carriers. Those compositions contain a pesticidally effective amount of said compound or compounds, which amount may vary depending upon the particular compound, target pest, and method of use. Those skilled in the art can readily determine what is a pesticidally effective amount without undue experimentation.

This invention also provides a method for treating, controlling, preventing and protecting warm-blooded animals, including humans and fish against infestation and infection by helminths which comprises orally, topically or parenterally administering or applying to said animals an anthelmintically effective amount of a 1-aryl-1-(substituted thio, sulfinyl or sulfonyl)-2-nitroethane compound of formula I.

The above method is particularly useful for controlling and preventing parasitic helminth infections in animals such as cattle, sheep, swine, camels, deer, horses, poultry, fish, rabbits, goats, dogs and cats as well as humans.

Helminthiasis is a widespread disease found in many farm and companion animals and is responsible for significant economic losses throughout the world. Among the helminths causing significant damage are members of the class Trematoda, commonly known as flukes or flatworms, especially members of the genera Fasciola, Fascioloides, Paramphistomum, Dicrocoelium, Eurytrema, Ophisthorchis, Fasciolopsis, Echinostoma, Paragonimus and the like. Helminthiasis is also caused by a group of worms referred to as nematodes. Nematodes cause serious damage to the walls and tissues of the organs in which they reside, including the intestinal tract, heart, lungs and blood vessels, and are a primary cause of anemia. If left untreated they may result in death to the infected animals. Nematodes commonly found to be the infecting agents of warm-blooded animals include the genera Haemonchus, Ostertagia, Cooperia, Oesphagastomum, Nematodirus, Dictyocaulus, Trichuris, Dirofilaria, Ancyclostoma, Ascaris and the like. Advantageously, the formula I compounds of this invention are useful against the causative agents of helminthiases.

For oral administration to warm-blooded animals, the formula I compounds may be formulated as animal feeds, animal feed premixes, animal feed concentrates, pills, pastes, suspensions, solutions, gels, tablets, boluses and capsules. In addition, the formula I compounds may be administered to the animals in their drinking water. For oral administration, the dosage form chosen should provide the animal with about 0.01 mg/kg to 100 mg/kg of animal body weight per day of the formula I compound.

Alternatively, the formula I compounds may be administered to animals parenterally, for example, by intraruminal, intramuscular, intravenous or subcutaneous injection or by transdermal methods. The formula I compounds may be dispersed or dissolved in a physiologically acceptable carrier for injection or transdermal application Alternatively, the formula I compounds may be formulated into an implant for subcutaneous administration. For parenteral administration, the dosage form chosen should provide the animal with about 0.01 mg/kg to 100 mg/kg of animal body weight per day of the formula I compound.

The formula I compounds may also be applied topically to the animals in the form of dips, dusts, collars, medallions, sprays and pour-on formulations. For topical application, dips and sprays usually contain about 0.5 ppm to 5,000 ppm and preferably about 1 ppm to 3,000 ppm of the formula I compound. In addition, the formula I compounds may be formulated as ear tags for animals, particularly quadrupeds such as cattle and sheep.

The formula I compounds of this invention may also be used in combination or conjunction with one or more other parasiticidal compounds including, but not limited to, anthelmintics, such as benzimidazoles, piperazine, levamisole, pyrantel, praziquantel and the like; endectocides such as avermectins, milbemycins and the like; ectoparasiticides such as arylpyrroles, organophosphates, carbamates, gamabutyric acid inhibitors including fipronil, pyrethroids, spinosads, imidacloprid and the like; insect growth regulators such as pyriproxyfen, cyromazine and the like; and chitin synthase inhibitors such as benzoylureas including flufenoxuron.

The formula I compounds may also be used in combination or conjunction with one or more conventional synergists such as piperonyl butoxide, N-octyl bicycloheptene dicarboximide, dipropyl pyridine-2,5-dicarboxylate and 1,5a,6,9,9a,9b-hexahydro-4a(4H)-dibenzofurancarboxaldehyde to enhance efficacy, broaden spectrum and provide a convenient method for parasite control.

The parasiticidal compositions of the present invention include a formula I compound of this invention (or combinations thereof) admixed with one or more pharmaceutically and/or agronomically acceptable inert, solid or liquid carriers. Those compositions contain a parasiticidally effective amount of said compound or compounds. Those skilled in the art can readily determine what is a parasiticidally effective amount without undue experimentation.

The present invention also provides novel 1-aryl-1-(substituted thio, sulfinyl or sulfonyl)-2-nitroethane compounds having the structural formula Ia

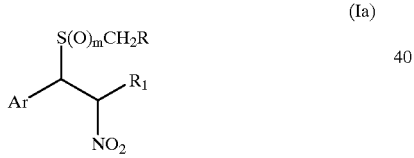

(Ia)

wherein
  Ar is phenyl optionally substituted with any combination of one to five halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups, one to three $C_1$–$C_4$halo-alkylthio groups, one benzylthio group or one $SCH_2CO_2R_2$ group,
    1- or 2-naphthyl optionally substituted with any combination of one to five halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups,
    piperonyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups,
    2-, 3- or 4-pyridyl optionally substituted with any combination of one to four halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups,
    2- or 3-furyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups, or
    2- or 3-thienyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups;
  R is hydrogen, $CO_2R_3$, $C(O)NR_4R_5$, $(CH_2)_nCR_2(NR_4R_5)$ $CO_2R_3$, $CH(OR_6)CH_2OR_7$, $CH(CH_2OR_8)SCH(R_9)$ $CH_2NO_2$, $C_1$–$C_4$alkyl, $C_1$–$C_4$haloalkyl, $C_2$–$C_4$alkenyl, $C_2$–$C_4$haloalkenyl,
    phenyl optionally substituted with any combination of one to five halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$halo-alkylthio groups,
    2- or 3-furyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups, or
    2- or 3-thienyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups;
  $R_2$, $R_6$, $R_7$ and $R_8$ are each independently hydrogen or $C_1$–$C_6$alkyl;
  m is 0, 1 or 2;
  n is 0 or 1;
  $R_9$ is phenyl optionally substituted with any combination of one to five halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$halo-alkylthio groups;
  $R_3$ is hydrogen, $C_1$–$C_{10}$alkyl, $CH_2(C_1$–$C_{10}$haloalkyl), $C_3$–$C_{10}$alkenyl, $C_3$–$C_{10}$haloalkenyl, a cation, benzyl optionally substituted on the ring with any combination of one to five halogen atoms, one or two cyano groups, one or two nitro groups, one to three $C_1$-$C_4$alkyl groups, one to three $C_1$-$C_4$haloalkyl groups, one to three $C_1$-$C_4$alkoxy groups, one to three $C_1$-$C_4$haloalkoxy groups, one to three $C_1$-$C_4$alkylthio groups or one to three $C_1$-$C_4$haloalkylthio groups, or phenyl optionally substituted with any combination of one to five halogen atoms, one or two cyano groups, one or two nitro groups, one to three $C_1$-$C_4$alkyl groups, one to three $C_1$-$C_4$haloalkyl groups, one to three $C_1$-$C_4$alkoxy groups, one to three $C_1$-$C_4$haloalkoxy groups, one to three $C_1$-$C_4$alkylthio groups or one to three $C_1$-$C_4$haloalkylthio groups;

$R_4$ and $R_5$ are each independently hydrogen, $C_1$-$C_{10}$alkyl, $CH_2(C_1$-$C_{10}$haloalkyl$)$, $C_3$-$C_{10}$alkenyl, $C_3$-$C_{10}$haloalkenyl, benzyl optionally substituted on the ring with any combination of one to five halogen atoms, one or two cyano groups, one or two nitro groups, one to three $C_1$-$C_4$alkyl groups, one to three $C_1$-$C_4$haloalkyl groups, one to three $C_1$-$C_4$alkoxy groups, one to three $C_1$-$C_4$haloalkoxy groups, one to three $C_1$-$C_4$alkylthio groups or one to three $C_1$-$C_4$haloalkylthio groups, or phenyl optionally substituted with any combination of one to five halogen atoms, one or two cyano groups, one or two nitro groups, one to three $C_1$-$C_4$alkyl groups, one to three $C_1$-$C_4$haloalkyl groups, one to three $C_1$-$C_4$alkoxy groups, one to three $C_1$-$C_4$haloalkoxy groups, one to three $C_1$-$C_4$alkylthio groups or one to three $C_1$-$C_4$haloalkylthio groups, and when $R_4$ and $R_5$ are taken together with the atom to which they are attached, they may form a five- or six-membered ring wherein $R_4R_5$ is represented by: —$(CH_2)_4$—, —$(CH_2)_5$— or —$(CH_2)_2O(CH_2)_2$—; and $R_1$ is hydrogen, $C_1$-$C_4$alkyl or phenyl optionally substituted with any combination of one to five halogen atoms, one or two cyano groups, one or two nitro groups, one to three $C_1$-$C_4$alkyl groups, one to three $C_1$-$C_4$haloalkyl groups, one to three $C_1$-$C_4$alkoxy groups, one to three $C_1$-$C_4$haloalkoxy groups, one to three $C_1$-$C_4$alkylthio groups or one to three $C_1$-$C_4$haloalkylthio groups; and provided that Ar is other than phenyl optionally substituted with any combination of one to three halogen atoms, one or two nitro groups, one or two cyano groups, one to three $C_1$-$C_4$alkyl groups, one to three $C_1$-$C_4$haloalkyl groups, one to three $C_1$-$C_4$alkoxy groups or one to three $C_1$-$C_4$haloalkoxy groups when R is: (1) $CO_2R_3$ and $R_3$ is hydrogen or $C_1$-$C_{10}$alkyl, (2) $C_1$-$C_4$alkyl, or (3) phenyl optionally substituted with one to five halogen atoms.

Exemplary of halogen hereinabove are fluorine, chlorine, bromine and iodine. The terms "$C_1$-$C_4$haloalkyl", "$C_1$-$C_{10}$haloalkyl", "$C_1$-$C_4$haloalkoxy", "$C_1$-$C_4$haloalkylthio", "$C_2$-$C_4$haloalkenyl" and "$C_3$-$C_{10}$haloalkenyl" are defined as a $C_1$-$C_4$alkyl group, a $C_1$-$C_{10}$alkyl group, a $C_1$-$C_4$alkoxy group, a $C_1$-$C_4$alkylthio group, a $C_2$-$C_4$alkenyl group and a $C_3$-$C_{10}$alkenyl group substituted with one or more halogen atoms, respectively. As used in formulas I and Ia above, cation designates alkali metals, alkaline earth metals, manganese, copper, iron, zinc, cobalt, lead, silver, nickel, ammonium or organic ammonium. Alkali metals include sodium, potassium and lithium. Alkaline earth metals include calcium and magnesium. Organic ammonium cations include, but are not limited to, monoalkylammonium, dialkylammonium, trialkylammonium, tetraalkylammonium, monoalkenylammonium, dialkenylammonium, trialkenylammonium, monoalkynylammonium, dialkynylammonium, monoalkanolammonium, dialkanolammonium, $C_5$-$C_6$cycloalkylammonium, piperidinium, morpholinium, pyrrolidinium, benzylammonium and the like.

The formula I compounds of this invention wherein m is 0 may be prepared by reacting a 1-aryl-2-nitroethylene compound having the structural formula II with a substituted thiol compound having the structural formula III and a base in the presence of a solvent as shown below in Flow Diagram I.

FLOW DIAGRAM I

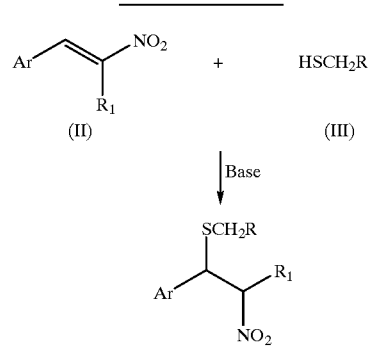

Formula I compounds wherein m is 1 or 2 may be prepared, as shown in Flow Diagram II, by oxidizing a formula I compound wherein m is 0 with conventional oxidizing agents such as 3-Chloroperoxybenzoic acid and the like in the presence of a solvent.

FLOW DIAGRAM II

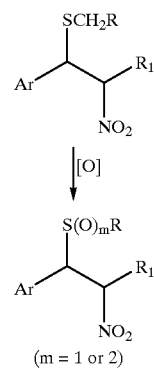

(m = 1 or 2)

In addition, certain compounds of formula I may be converted into other compounds of formula I by using conventional procedures known to those skilled in the art.

Starting 1-aryl-2-nitroethylene compounds of formula II are known in the art and may be prepared by the procedures described by R. Jacobo et al in Journal of Fluorine Chemistry, 67 pp. 253–255 (1994) and A. Jara et al in Synthetic Communications, 24(3), pp. 417–426 (1994).

The formula III substituted thiol compounds are also known in the art and may be prepared according to the procedures described by Baker et al in Journal of Organic Chemistry, 12, pp. 138–154 (1947).

In order to facilitate a further understanding of the invention, the following examples are presented to illustrate more specific details thereof. The invention is not to be limited thereby except as defined in the claims.

EXAMPLES 1–205

Preparation of {[alpha-(nitromethyl)benzyl]thio}-acetic acid

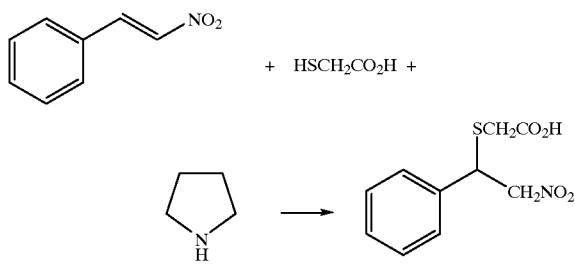

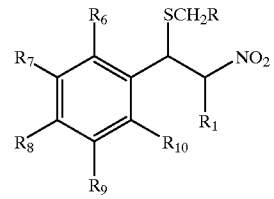

A solution of nitrostyrene (10 g, 0.067 mol) in tetrahydrofuran (250 ml) is treated with mercaptoacetic acid (7.4 g, 5.6 ml, 0.08 mol) followed by pyrollidine (3 drops). After stirring for 2 hours the reaction mixture is concentrated onto silica gel and chromatographed, eluting with 4:1, hexanes-:ethyl acetate, to give the title product as a solid (13.14 g, 81% yield). Analysis: $C_8H_7NO_2$. Calculated: C, 49.78; H, 4.60; N, 5.81%. Found: C, 49.50; H, 4.66; N, 5.81%.

Following essentially the same procedure as described in example 1, but using the appropriately substituted nitro and thiol compounds, the following compounds are obtained:

| Example | $R_6$ | $R_7$ | $R_8$ | $R_9$ | $R_{10}$ | R | $R_1$ | Color/State |
|---|---|---|---|---|---|---|---|---|
| 2 | H | H | H | H | H | $CH=CH_2$ | H | Yellow oil |
| 3 | H | $OCH_3$ | H | $OCH_3$ | H | $CH=CH_2$ | H | Yellow oil |
| 4 | H | H | H | H | H | $CO_2CH_3$ | H | Yellow oil |
| 5 | H | H | $CH_3$ | H | H | $CO_2C_2H_5$ | H | Colorless oil |
| 6 | H | H | H | H | H | $CO_2C_2H_5$ | H | Colorless oil |
| 7 | H | H | H | H | H | $CO_2(CH_2)_3CH_3$ | H | Colorless oil |
| 8 | H | H | H | H | H | $CO_2(CH_2)_5CH(CH_3)_2$ | H | Colorless oil |
| 9 | H | H | H | H | H | $CO_2CH_2CH(C_2H_5)[(CH_2)_3CH_3]$ | H | Colorless oil |
| 10 | H | H | H | H | H | $C_6H_5$ | H | Colorless oil |
| 11 | H | H | F | H | H | $CO_2(CH_2)_5CH(CH_3)_2$ | H | Colorless oil |
| 12 | H | H | F | H | H | $CO_2CH_2CH(C_2H_5)[(CH_2)_3CH_3]$ | H | Colorless oil |
| 13 | H | H | F | H | H | $C_6H_5$ | H | Colorless oil |
| 14 | H | H | F | H | H | $C_2H_5$ | H | Colorless oil |
| 15 | H | H | F | H | H | $CO_2CH_3$ | H | Colorless oil |
| 16 | H | H | F | H | H | $CO_2C_2H_5$ | H | Colorless oil |
| 17 | H | H | F | H | H | $CO_2(CH_2)_3CH_3$ | H | Colorless oil |
| 18 | H | H | —$OCH_2O$— | | H | $CO_2CH_3$ | H | Yellow oil |
| 19 | H | H | —$OCH_2O$— | | H | $CO_2C_2H_5$ | H | Yellow oil |
| 20 | H | H | —$OCH_2O$— | | H | $CO_2(CH_2)_3CH_3$ | H | Yellow liquid |
| 21 | H | H | —$OCH_2O$— | | H | $CO_2(CH_2)_5CH(CH_3)_2$ | H | Yellow oil |
| 22 | H | H | —$OCH_2O$— | | H | $CO_2CH_2CH(C_2H_5)[(CH_2)_3CH_3]$ | H | Yellow oil |
| 23 | H | H | —$OCH_2O$— | | H | $C_6H_5$ | H | Yellow oil |
| 24 | H | H | —$OCH_2O$— | | H | $C_2H_5$ | H | Yellow oil |
| 25 | H | H | $CH_3$ | H | H | H | H | Tan oil |
| 26 | H | H | $CH_3$ | H | H | H | H | Colorless oil |
| 27 | H | H | $CH_3$ | H | H | H | H | Colorless oil |
| 28 | H | H | $CH_3$ | H | H | H | H | Yellow oil |
| 29 | H | H | $CH_3$ | H | H | H | H | Yellow oil |
| 30 | H | H | $CH_3$ | H | H | H | H | Yellow oil |
| 31 | H | H | $CH(CH_3)_2$ | H | H | H | H | Yellow oil |
| 32 | H | H | $CH(CH_3)_2$ | H | H | H | H | Yellow oil |
| 33 | H | H | $CH(CH_3)_2$ | H | H | H | H | Yellow oil |
| 34 | H | H | $CH(CH_3)_2$ | H | H | H | H | Yellow oil |
| 35 | H | H | $CH(CH_3)_2$ | H | H | H | H | Yellow oil |
| 36 | H | H | $CH(CH_3)_2$ | H | H | $C_6H_5$ | H | Yellow oil |
| 37 | H | H | $CH(CH_3)_2$ | H | H | $C_2H_5$ | H | Yellow oil |
| 38 | H | H | $CH(CH_3)_2$ | H | H | $CH=CH_2$ | H | Yellow oil |
| 39 | H | H | H | H | F | $CO_2CH_3$ | H | Yellow oil |
| 40 | H | H | H | H | F | $CO_2C_2H_5$ | H | Yellow oil |
| 41 | H | H | H | H | F | $CO_2(CH_2)_3CH_3$ | H | Yellow oil |
| 42 | H | H | H | H | F | $CO_2(CH_2)_5CH(CH_3)_2$ | H | Yellow oil |
| 43 | H | H | H | H | F | $CO_2CH_2CH(C_2H_5)[(CH_2)_3CH_3]$ | H | Yellow oil |
| 44 | H | H | H | H | F | $C_6H_5$ | H | Yellow oil |

-continued

| | | | | | | | | |
|---|---|---|---|---|---|---|---|---|
| 45 | H | H | H | H | F | $C_2H_5$ | H | Yellow oil |
| 46 | H | H | H | H | F | $CH=CH_2$ | H | Yellow oil |
| 47 | H | H | $OCH_3$ | H | H | $CO_2CH_3$ | H | Yellow oil |
| 48 | H | H | $OCH_3$ | H | H | $CO_2C_2H_5$ | H | Yellow oil |
| 49 | H | H | $OCH_3$ | H | H | $CO_2(CH_2)_3CH_3$ | H | Yellow oil |
| 50 | H | H | $OCH_3$ | H | H | $CO_2(CH_2)_5CH(CH_3)_2$ | H | Yellow oil |
| 51 | H | H | $OCH_3$ | H | H | $CO_2CH_2CH(C_2H_5)[(CH_2)_3CH_3]$ | H | Yellow oil |
| 52 | H | H | $OCH_3$ | H | H | $C_6H_5$ | H | Yellow oil |
| 53 | H | H | $OCH_3$ | H | H | $C_2H_5$ | H | Yellow oil |
| 54 | H | H | $OCH_3$ | H | H | $CH=CH_2$ | H | Yellow oil |
| 55 | H | H | H | $OCH_3$ | H | $CO_2CH_3$ | H | Yellow oil |
| 56 | H | H | H | $OCH_3$ | H | $CO_2C_2H_5$ | H | Yellow oil |
| 57 | H | H | H | $OCH_3$ | H | $CO_2(CH_2)_3CH_3$ | H | Yellow oil |
| 58 | H | H | H | $OCH_3$ | H | $CO_2(CH_2)_5CH(CH_3)_2$ | H | Yellow oil |
| 59 | H | H | H | $OCH_3$ | H | $CO_2CH_2CH(C_2H_5)[(CH_2)_3CH_3]$ | H | Yellow oil |
| 60 | H | H | H | $OCH_3$ | H | $C_6H_5$ | H | Yellow oil |
| 61 | H | H | H | $OCH_3$ | H | $C_2H_5$ | H | Yellow oil |
| 62 | H | H | H | $OCH_3$ | H | $CH=CH_2$ | H | Yellow oil |
| 63 | H | H | F | H | H | $CO_2H$ | H | Brown oil |
| 64 | H | H | —$OCH_2O$— | | H | $CO_2H$ | H | Brown oil |
| 65 | H | H | $CH_3$ | H | H | $CO_2H$ | H | Off-white semi-solid |
| 66 | H | H | $CH(CH_3)_2$ | H | H | $CO_2H$ | H | Brown oil |
| 67 | H | H | H | H | F | $CO_2H$ | H | Brown oil |
| 68 | H | H | H | $OCH_3$ | H | $CO_2H$ | H | Brown oil |
| 69 | H | H | $OCH_3$ | H | H | $CO_2H$ | H | Brown oil |
| 70 | H | H | Cl | H | H | $CO_2CH_3$ | H | Yellow oil |
| 71 | H | H | Cl | H | H | $CO_2C_2H_5$ | H | Yellow oil |
| 72 | H | H | Cl | H | H | $CO_2(CH_2)_3CH_3$ | H | Yellow oil |
| 73 | H | H | Cl | H | H | $CO_2(CH_2)_5CH(CH_3)_2$ | H | Yellow oil |
| 74 | H | H | Cl | H | H | $CO_2CH_2CH(C_2H_5)[(CH_2)_3CH_3]$ | H | Yellow oil |
| 75 | H | H | Cl | H | H | $C_6H_5$ | H | Yellow oil |
| 76 | H | H | Cl | H | H | $C_2H_5$ | H | Yellow oil |
| 77 | H | H | Cl | H | H | $CH=CH_2$ | H | Yellow oil |
| 78 | H | H | Cl | H | H | $CO_2H$ | H | Yellow oil |
| 79 | H | H | $OCH_3$ | H | $OCH_3$ | $CO_2CH_3$ | H | Yellow |
| 80 | H | H | $OCH_3$ | H | $OCH_3$ | $C(O)-N\underset{\diagdown}{\diagup}O$ (morpholine) | H | White |
| 81 | H | H | $OCH_3$ | H | $OCH_3$ | $C_6H_5$ | H | Yellow |
| 82 | H | H | H | H | H | $CHSCHCH_2NO_2$ with $C_6H_5$ and $CH_2OH$ substituents | H | White oil |
| 83 | H | H | H | H | H | $CH(NH_2)CO_2H$ | H | White |
| 84 | H | H | $OCH_3$ | H | $OCH_3$ | $CH(NH_2)CO_2H$ | H | Yellow |
| 85 | H | H | H | H | H | $CH(OH)(CH_2OH)$ | H | Yellow oil |
| 86 | H | H | $OCH_3$ | $OCH_3$ | H | $CO_2CH_3$ | H | Yellow |
| 87 | H | $OCH_3$ | H | $OCH_3$ | H | $CH(OH)(CH_2OH)$ | H | Yellow oil |
| 88 | H | H | H | H | Cl | $CO_2CH_3$ | H | Yellow oil |
| 89 | H | H | H | H | Cl | $CO_2C_2H_5$ | H | Yellow oil |
| 90 | H | H | H | H | Cl | $CO_2(CH_2)_3CH_3$ | H | Yellow oil |
| 91 | H | H | H | H | Cl | $CO_2(CH_2)_5CH(CH_3)_2$ | H | Yellow oil |
| 92 | H | H | H | H | Cl | $CO_2CH_2CH(C_2H_5)[(CH_2)_3CH_3]$ | H | Yellow oil |
| 93 | H | H | H | H | Cl | $C_6H_5$ | H | Yellow oil |
| 94 | H | H | H | H | Cl | $C_2H_5$ | H | Yellow oil |
| 95 | H | H | H | H | Cl | $CH=CH_2$ | H | Yellow oil |
| 96 | H | H | H | H | Cl | $CO_2H$ | H | Off-white semi-solid |
| 97 | H | H | H | H | H | $CH_3$ | H | Yellow oil |
| 98 | H | H | H | CN | H | $CO_2CH_3$ | H | Brown semi-solid |
| 99 | H | H | H | CN | H | $CO_2C_2H_5$ | H | Colorless oil |
| 100 | H | H | H | CN | H | $CO_2(CH_2)_2CH_3$ | H | Colorless oil |
| 101 | H | H | H | CN | H | $CO_2(CH_2)_3CH_3$ | H | Tan oil |
| 102 | H | H | $OCH_3$ | H | H | $CO_2(CH_2)_2CH_3$ | H | Tan oil |
| 103 | H | H | H | $OCH_3$ | H | $CO_2(CH_2)_2CH_3$ | H | Tan semi-solid |
| 104 | H | H | —$OCH_2O$— | | H | $CO_2(CH_2)_2CH_3$ | H | Tan oil |
| 105 | H | H | H | H | H | $CO_2(CH_2)_2CH_3$ | H | Colorless oil |
| 106 | H | H | —$OCH_2O$— | | H | $CO_2CH_2C_6H_5$ | H | Tan oil |
| 107 | H | H | H | $OCH_3$ | H | $CO_2CH_2C_6H_5$ | H | Tan oil |
| 108 | H | H | $OCH_3$ | H | H | $CO_2CH_2C_6H_5$ | H | Tan oil |
| 109 | H | H | —CH=CH—CH=CH— | | H | $CO_2H$ | H | Lt. yellow semi-solid |
| 110 | H | H | —CH=CH—CH=CH— | | H | $CO_2CH_3$ | H | Lt. yellow oil |

-continued

| | | | | | | | | |
|---|---|---|---|---|---|---|---|---|
| 111 | H | H | —CH=CH—CH=CH— | | H | $CO_2C_2H_5$ | H | Lt. yellow oil |
| 112 | H | H | —CH=CH—CH=CH— | | H | $CO_2(CH_2)_2CH_3$ | H | Lt. yellow oil |
| 113 | H | H | —CH=CH—CH=CH— | | H | $CO_2(CH_2)_3CH_3$ | H | Lt. yellow oil |
| 114 | H | H | —CH=CH—CH=CH— | | H | $CO_2CH_2C_6H_5$ | H | Lt. yellow oil |
| 115 | H | H | —CH=CH—CH=CH— | | H | $C_2H_5$ | H | Lt. yellow solid |
| 116 | H | H | —CH=CH—CH=CH— | | H | $C_6H_5$ | H | Lt. yellow solid |
| 117 | H | H | $OCF_3$ | H | H | $CO_2CH_3$ | H | Lt. yellow oil |
| 118 | H | H | $OCF_3$ | H | H | $CO_2C_2H_5$ | H | Lt. yellow oil |
| 119 | H | H | $OCF_3$ | H | H | $CO_2(CH_2)_2CH_3$ | H | Lt. yellow oil |
| 120 | H | H | $OCF_3$ | H | H | $CO_2(CH_2)_3CH_3$ | H | Lt. yellow oil |
| 121 | H | H | $OCF_3$ | H | H | $CO_2CH_2C_6H_5$ | H | Lt. yellow oil |
| 122 | H | H | $OCF_3$ | H | H | $C_2H_5$ | H | Lt. yellow oil |
| 123 | H | H | $OCF_3$ | H | H | $CH=CH_2$ | H | Lt. yellow oil |
| 124 | H | H | $OCF_3$ | H | H | $C_6H_5$ | H | Lt. yellow oil |
| 125 | H | H | —CH=CH—CH=CH— | | H | $CH=CH_2$ | H | Lt. yellow solid |
| 126 | H | H | H | H | H | H | $C_6H_5$ | |
| 127 | H | H | $OCF_3$ | H | H | $CO_2H$ | H | Lt. colorless solid |
| 128 | H | H | H | $NO_2$ | H | $CO_2H$ | H | Dk. yellow semi-solid |
| 129 | H | H | H | $NO_2$ | H | $CH=CH_2$ | H | Dk. yellow oil |
| 130 | Cl | H | H | H | Cl | $CO_2H$ | H | Colorless semi-solid |
| 131 | Cl | H | H | H | Cl | $CO_2CH_3$ | H | Colorless oil |
| 132 | Cl | H | H | H | Cl | $CO_2C_2H_5$ | H | Colorless oil |
| 133 | Cl | H | H | H | Cl | $CO_2(CH_2)_2CH_3$ | H | Colorless oil |
| 134 | Cl | H | H | H | Cl | $CO_2(CH_2)_3CH_3$ | H | Colorless oil |
| 135 | Cl | H | H | H | Cl | $CO_2CH_2C_6H_5$ | H | Colorless oil |
| 136 | Cl | H | H | H | Cl | $C_2H_5$ | H | Lt. yellow oil |
| 137 | Cl | H | H | H | Cl | $C_6H_5$ | H | Colorless oil |
| 138 | H | H | H | $NO_2$ | H | $CO_2CH_3$ | H | Lt. yellow oil |
| 139 | F | F | F | F | F | $CO_2H$ | H | Yellow oil |
| 140 | F | F | F | F | F | $CO_2CH_3$ | H | Dk. yellow oil |
| 141 | F | F | $SCH_2CO_2$—$CH_3$ | F | F | $CO_2CH_3$ | H | Yellow semi-solid |
| 142 | F | F | F | F | F | $CO_2C_2H_5$ | H | Yellow oil |
| 143 | F | F | $SCH2CO_2$—$C_2H_5$ | F | F | $CO_2C_2H_5$ | H | Yellow oil |
| 144 | F | F | F | F | F | $CO_2(CH_2)_2CH_3$ | H | Dk. yellow oil |
| 145 | F | F | $SCH_2CO_2$—$(CH_2)_2CH_3$ | F | F | $CO_2(CH_2)_2CH_3$ | H | Dk. yellow oil |
| 146 | F | F | F | F | F | $CO_2(CH_2)_3CH_3$ | H | Yellow oil |
| 147 | F | F | $SCH_2CO_2$—$(CH_2)_3CH_3$ | F | F | $CO_2(CH_2)_3CH_3$ | H | Yellow oil |
| 148 | F | F | F | F | F | $C_6H_5$ | H | Dk. yellow semi-solid |
| 149 | F | F | $SCH_2C_6H_5$ | F | F | $C_6H_5$ | H | Yellow oil |
| 150 | H | H | H | H | H | $CO_2CH_3$ | $CH_3$ | Yellow oil |
| 151 | H | H | H | H | H | $CO_2C_2H_5$ | $CH_3$ | Yellow oil |
| 152 | H | H | F | F | H | $CO_2CH_3$ | H | Yellow oil |
| 153 | H | H | F | F | H | $CO_2C_2H_5$ | H | Yellow oil |
| 154 | H | H | F | F | H | $CO_2(CH_2)_2CH_3$ | H | Yellow oil |
| 155 | H | H | F | F | H | $CO_2CH(CH_3)_2$ | H | Yellow oil |
| 156 | H | H | H | H | H | 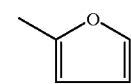 | H | Tan oil |
| 157 | H | H | $OCH_3$ | H | H | 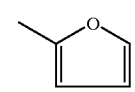 | H | Tan oil |
| 158 | H | H | H | $OCH_3$ | H | 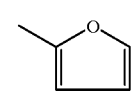 | H | Tan oil |
| 159 | H | H | —$OCH_2O$— | | H | 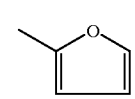 | H | Colorless oil |
| 160 | H | H | H | H | H | 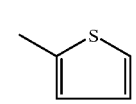 | H | Colorless oil |
| 161 | H | H | H | H | H | $CO_2H$ | $CH_3$ | Colorless oil |
| 162 | H | H | H | H | H | $CO_2(CH_2)_3CH_3$ | $CH_3$ | Tan oil |
| 163 | H | H | $NO_2$ | H | H | $CO_2H$ | H | Yellow solid |

| | | | | | | | | |
|---|---|---|---|---|---|---|---|---|
| 164 | H | H | NO$_2$ | H | H | CO$_2$CH$_3$ | H | Yellow oil |
| 165 | H | H | NO$_2$ | H | H | CO$_2$C$_2$H$_5$ | H | Yellow oil |
| 166 | H | H | NO$_2$ | H | H | CO$_2$(CH$_2$)$_2$CH$_3$ | H | Yellow oil |
| 167 | H | H | NO$_2$ | H | H | CO$_2$(CH$_2$)$_3$CH$_3$ | H | Yellow oil |
| 168 | H | H | NO$_2$ | H | H | C$_2$H$_5$ | H | Yellow solid |
| 169 | H | H | NO$_2$ | H | H | CH=CH$_2$ | H | Yellow semi-solid |
| 170 | H | H | NO$_2$ | H | H | C$_6$H$_5$ | H | Yellow solid |

| Example | R | Color/State |
|---|---|---|
| 171 | CO$_2$CH$_3$ | Dark orange oil |
| 172 | CO$_2$C$_2$H$_5$ | Light red oil |
| 173 | CO$_2$(CH$_2$)$_2$CH$_3$ | Light orange oil |
| 174 | CO$_2$CH$_2$C$_6$H$_5$ | Dark red oil |
| 175 | C$_2$H$_5$ | Light orange oil |
| 176 | CH=CH$_2$ | Light red oil |
| 177 | C$_6$H$_5$ | Dark orange oil |
| 178 | CO$_2$(CH$_2$)$_2$CH$_3$ | Light orange oil |
| 179 | CO$_2$H | Light yellow semi-solid |

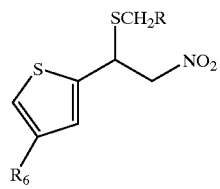

| Example | R$_6$ | R | Color/State |
|---|---|---|---|
| 180 | H | CH$_3$ | Orange Oil |
| 181 | H | CO$_2$H | Dark orange oil |
| 182 | H | CO$_2$CH$_3$ | Light yellow oil |
| 183 | H | CO$_2$C$_2$H$_5$ | Light yellow oil |
| 184 | H | CO$_2$(CH$_2$)$_3$CH$_3$ | Light yellow oil |
| 185 | H | CO$_2$CH$_2$C$_6$H$_5$ | Light yellow oil |
| 186 | H | C$_2$H$_5$ | Light orange liquid |
| 187 | H | CH=CH$_2$ | Light orange liquid |
| 188 | H | C$_6$H$_5$ | Light orange oil |
| 189 | H | CO$_2$(CH$_2$)$_2$CH$_3$ | Light yellow oil |
| 190 | Br | CO$_2$H | Light brown oil |
| 191 | Br | CO$_2$CH$_3$ | Light brown oil |
| 192 | Br | CO$_2$C$_2$H$_5$ | Yellow oil |
| 193 | Br | CO$_2$(CH$_2$)$_2$CH$_3$ | Yellow oil |
| 194 | Br | CO$_2$(CH$_2$)$_3$CH$_3$ | Yellow oil |
| 195 | Br | C$_6$H$_5$ | Yellow oil |

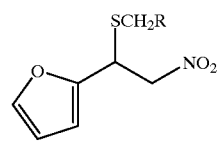

| Example | R | Color/State |
|---|---|---|
| 196 | CO$_2$H | Dark orange oil |
| 197 | CO$_2$CH$_3$ | Light yellow oil |
| 198 | CO$_2$C$_2$H$_5$ | Light yellow oil |
| 199 | CO$_2$(CH$_2$)$_2$CH$_3$ | Light yellow oil |
| 200 | CO$_2$(CH$_2$)$_3$CH$_3$ | Light yellow oil |
| 201 | C$_2$H$_5$ | Dark yellow oil |
| 202 | CH=CH$_2$ | Light yellow oil |
| 203 | C$_6$H$_5$ | Colorless oil |

EXAMPLE 204

Soil Nematicide Assay Targeting Root-knot Nematode, Meloidogyne Incognita on Potted Tomato The test compound is solubilized in acetone and diluted with water to the required test concentration. Silty loam soil in a 3 inch pot with a 3-week-old tomato transplant is drenched with the test solution. Four thousand root-knot nematode *Meloidogyne incognita* J2 larvae are dispensed in a aqueous suspension onto the soil. The pots are kept in the greenhouse and 4 weeks following inoculation of the pots, plant roots are washed free of soil and scored for the degree of root galling using the root-knot galling index identified below. Ethoprophos is included in the test as an industrial standard. The results are summarized in Table I

Root-Knot Galling Index

| Galling Index | Percentage of total root system galled |
|---|---|
| 0 | 0 |
| 1 | 10 |
| 2 | 20 |
| 3 | 30 |
| 4 | 40 |
| 5 | 50 |
| 6 | 60 |
| 7 | 70 |
| 8 | 80 |
| 9 | 90 |
| 10 | 100 |

TABLE I

Soil Nematicide Evaluations

| Compound | Rate (ppm) | Galling Index |
|---|---|---|
| Example 1 | 50 | 0 |
|  | 25 | 0 |
|  | 10 | 1 |
| Ethoprophos | 50 | 0[1] |
|  | 25 | 0[1] |
|  | 10 | 0 |
| Check | — | 7 |

[1]Phytotoxicity observed

EXAMPLE 205

Evaluation of Test Compounds Against *M. incognita* (Root Knot Nematode)

Newly emerged *M. incognita* larvae are suspended in S Medium (buffered salt solution) to a concentration of 50-65 worms per 50 μl. 50 μl of the worm suspension are pipetted into microtiter plate wells containing the test compounds. The plates are then covered with plactic plate sealers to reduce loss of volume by evaporation. After 20–24 hours of incubation, the larvae are scored for movement. Wells containing obviously dead/paralyzed larvae are scored as positive. A score of "9" indicates inactive worms with a straight, sticklike morphology. A score of "8" indicates inactive worms with a limp, curled or curved morphology. A score of "7" indicates dead/paralyzed worms after 72 hours. The results are summarized in Table II.

TABLE II

Nematicidal Evaluation of Test Compounds

| Example | *M. incognita* (150 ppm) |
|---|---|
| 1 | 9 |
| 2 | 9 |
| 4 | 9 |
| 5 | 9 |
| 6 | 9 |
| 7 | 9 |
| 8 | 0 |
| 9 | 0 |
| 10 | 0 |
| 11 | 0 |
| 12 | 0 |
| 13 | 0 |
| 14 | 0 |
| 15 | 9 |
| 16 | 9 |
| 17 | 9 |
| 18 | 9 |
| 19 | 9 |
| 20 | 9 |
| 21 | 8 |
| 22 | 0 |
| 23 | 8 |
| 24 | 9 |
| 25 | 9 |
| 26 | 9 |
| 27 | 0 |
| 28 | 9 |
| 29 | 9 |
| 30 | 0 |
| 31 | 9 |
| 32 | 9 |
| 33 | 0 |
| 34 | 0 |
| 35 | 0 |
| 36 | 0 |
| 37 | 0 |
| 38 | 0 |
| 39 | 9 |
| 40 | 9 |
| 41 | 9 |
| 42 | 0 |
| 43 | 0 |
| 44 | 0 |
| 45 | 0 |
| 46 | 9 |
| 47 | 9 |
| 48 | 9 |
| 49 | 9 |
| 50 | 0 |
| 51 | 0 |
| 52 | 9 |
| 53 | 9 |
| 54 | 9 |
| 55 | 9 |
| 56 | 9 |
| 57 | 9 |
| 58 | 0 |
| 59 | 0 |
| 60 | 0 |
| 61 | 0 |
| 62 | 9 |
| 63 | 9 |
| 64 | 9 |
| 65 | 9 |
| 66 | 9 |
| 67 | 9 |
| 68 | 9 |
| 69 | 9 |
| 70 | 9 |
| 71 | 0 |
| 72 | 0 |
| 73 | 0 |
| 74 | 0 |
| 75 | 0 |

TABLE II-continued

Nematicidal Evaluation of Test Compounds

| Example | M. incognita (150 ppm) |
|---|---|
| 76 | 0 |
| 77 | 0 |
| 78 | 9 |
| 79 | 0 |
| 80 | 0 |
| 81 | 0 |
| 82 | 9 |
| 83 | 9 |
| 84 | 0 |
| 85 | 9 |
| 86 | 0 |
| 87 | 0 |
| 88 | 8 |
| 89 | 8 |
| 90 | 8 |
| 91 | 0 |
| 92 | 0 |
| 93 | 0 |
| 94 | 0 |
| 95 | 0 |
| 96 | 9 |
| 98 | 0 |
| 99 | 0 |
| 100 | 0 |
| 101 | 9 |
| 102 | 9 |
| 103 | 9 |
| 104 | 8 |
| 105 | 0 |
| 106 | 0 |
| 107 | 0 |
| 108 | 9 |
| 109 | 0 |
| 110 | 0 |
| 111 | 0 |
| 112 | 0 |
| 113 | 0 |
| 114 | 0 |
| 115 | 0 |
| 116 | 0 |
| 117 | 0 |
| 118 | 0 |
| 119 | 9 |
| 120 | 9 |
| 121 | 8 |
| 122 | 0 |
| 123 | 0 |
| 124 | 0 |
| 125 | 0 |
| 127 | 9 |
| 128 | 9 |
| 129 | 0 |
| 130 | 9 |
| 131 | 9 |
| 132 | 0 |
| 133 | 0 |
| 134 | 0 |
| 135 | 0 |
| 136 | 0 |
| 137 | 0 |
| 138 | 0 |
| 171 | 9 |
| 172 | 9 |
| 173 | 9 |
| 174 | 9 |
| 175 | 9 |
| 176 | 9 |
| 177 | 9 |
| 178 | 9 |
| 179 | 9 |
| 181 | 9 |
| 182 | 9 |
| 183 | 9 |
| 184 | 9 |
| 185 | 9 |
| 186 | 0 |
| 187 | 9 |
| 188 | 9 |
| 189 | 9 |
| 196 | 9 |
| 197 | 9 |
| 198 | 9 |
| 199 | 9 |
| 200 | 9 |
| 201 | 0 |
| 202 | 0 |

EXAMPLE 206

Evaluation of Test Compounds Against *C. elegans*

Cultures of *C. elegans* (Bristol strain from J. Lewis) are maintained on *E. coli* lawns on NG Agar Plates at 20° C. New cultures are established weekly. Nematodes for testing are washed from cultures using Na buffer. Compounds are dissolved in 80% acetone. The test material is micropipetted (25 μl) into a single well of a 96-well sterile tissue culture plate and the solvent allowed to evaporate. A freshly prepared volume (50 μl) of *C. elegans* in Na buffer is micropipetted into each treated well and several control wells per plate. Plates are incubated at 20° C. Observations for efficacy are made under a dissecting microscope at 4 and 24 hours post-immersion. Immediately prior to reading the plate, it is gently tapped to stimulate the movement of the worms. Activity is judged subjectively, but semi-quantitatively, based on the drug effects on motility of the adults and larvae. The criteria are as follows: 9=complete kill in 4 hours, 8=complete kill in 24 hours, 7=markedly reduced motility in approximately 95% of worms in 24 hours, and 0=normal motility, same as controls. The results are summarized in Table III.

TABLE III

Evaluation of Test Compounds against *C. elegans*

| Example | Rating Against C. elegans (150 ppm) |
|---|---|
| 1 | 9 |
| 2 | 0 |
| 3 | 0 |
| 4 | 9 |
| 5 | 9 |
| 6 | 8 |
| 7 | 8 |
| 8 | 0 |
| 9 | 0 |
| 10 | 0 |
| 11 | 0 |
| 12 | 0 |
| 13 | 8 |
| 14 | 0 |
| 15 | 9 |
| 16 | 8 |
| 17 | 8 |
| 18 | 9 |
| 19 | 9 |
| 20 | 8 |

TABLE III-continued

Evaluation of Test Compounds against *C. elegans*

| Example | Rating Against *C. elegans* (150 ppm) |
|---|---|
| 21 | 0 |
| 22 | 0 |
| 23 | 7 |
| 24 | 8 |
| 25 | 9 |
| 26 | 8 |
| 27 | 0 |
| 28 | 0 |
| 29 | 8 |
| 30 | 0 |
| 31 | 8 |
| 32 | 7 |
| 33 | 7 |
| 34 | 0 |
| 35 | 0 |
| 36 | 0 |
| 37 | 0 |
| 38 | 0 |
| 39 | 9 |
| 40 | 8 |
| 41 | 7 |
| 42 | 0 |
| 43 | 0 |
| 44 | 7 |
| 45 | 0 |
| 46 | 7 |
| 47 | 9 |
| 48 | 9 |
| 49 | 9 |
| 50 | 7 |
| 51 | 0 |
| 52 | 9 |
| 53 | 9 |
| 54 | 9 |
| 55 | 8 |
| 56 | 8 |
| 57 | 7 |
| 58 | 0 |
| 59 | 0 |
| 60 | 0 |
| 61 | 7 |
| 62 | 7 |
| 63 | 9 |
| 64 | 9 |
| 65 | 9 |
| 66 | 9 |
| 67 | 9 |
| 68 | 8 |
| 69 | 9 |
| 70 | 7 |
| 71 | 7 |
| 72 | 0 |
| 73 | 0 |
| 74 | 0 |
| 75 | 0 |
| 76 | 7 |
| 77 | 0 |
| 78 | 7 |
| 79 | 7 |
| 80 | 7 |
| 81 | 7 |
| 82 | 9 |
| 83 | 9 |
| 84 | 9 |
| 85 | 7 |
| 86 | 0 |
| 87 | 0 |
| 89 | 0 |
| 90 | 7 |
| 91 | 0 |
| 92 | 0 |
| 93 | 0 |
| 94 | 0 |
| 95 | 0 |
| 96 | 9 |
| 98 | 8 |
| 99 | 0 |
| 100 | 8 |
| 101 | 0 |
| 102 | 9 |
| 103 | 8 |
| 104 | 9 |
| 105 | 9 |
| 106 | 8 |
| 107 | 0 |
| 108 | 8 |
| 109 | 9 |
| 110 | 9 |
| 111 | 8 |
| 112 | 9 |
| 113 | 9 |
| 114 | 9 |
| 115 | 0 |
| 116 | 0 |
| 117 | 8 |
| 118 | 8 |
| 119 | 8 |
| 120 | 0 |
| 121 | 9 |
| 122 | 8 |
| 123 | 7 |
| 124 | 7 |
| 125 | 0 |
| 127 | 9 |
| 128 | 9 |
| 129 | 0 |
| 130 | 9 |
| 131 | 7 |
| 132 | 0 |
| 133 | 0 |
| 134 | 0 |
| 135 | 0 |
| 136 | 0 |
| 137 | 0 |
| 139 | 9 |
| 140 | 8 |
| 141 | 8 |
| 142 | 8 |
| 143 | 0 |
| 144 | 7 |
| 145 | 0 |
| 146 | 7 |
| 147 | 0 |
| 148 | 0 |
| 149 | 0 |
| 158 | 9 |
| 171 | 7 |
| 172 | 8 |
| 173 | 8 |
| 174 | 0 |
| 175 | 0 |
| 176 | 0 |
| 177 | 0 |
| 178 | 0 |
| 203 | 9 |

EXAMPLE 207

Insecticidal and Acaricidal Evaluation of Test Compounds

Test solutions are prepared by dissolving the test compound in a 35% acetone in water mixture to give a concentration of 10,000 ppm. Subsequent dilutions are made with water as needed.

Spodoptera eridania, 2nd Instar Larvae, Southern Armyworm (SAW)

A Sieva lima bean leaf expanded to 7–8 cm in length is dipped in the test solution with agitation for 3 seconds and allowed to dry in a hood. The leaf is then placed in a 100×10 mm petri dish containing a damp filter paper on the bottom and ten 2nd instar caterpillars. At 5 days, observations are made of mortality, reduced feeding, or any interference with normal molting.

Diabrotica virgifera virgifera Leconte, 2nd Instar Western Corn Rootworm (WCR)

One cc of fine talc is placed in a 30 mL wide-mouth screw-top glass jar. One mL of the appropriate acetone test solution is pipetted onto the talc so as to provide 1.25 mg of active ingredient per jar. The jars are set under a gentle air flow until the acetone is evaporated. The dried talc is loosened, 1 cc of millet seed is added to serve as food for the insects and 25 mL of moist soil is added to each jar. The jar is capped and the contents thoroughly mixed mechanically. Following this, ten 2nd instar rootworms are added to each jar and the jars are loosely capped to allow air exchange for the larvae. The treatments are held for 5 days when mortality counts are made. Missing larvae are presumed dead, since they decompose rapidly and cannot be found. The concentrations of active ingredient used in this test correspond approximately to 50 kg/ha.

Tetranychus urticae (OP-resistant strain), 2-spotted Spider Mite (TSM)

Sieva lima bean plants with primary leaves expanded to 7–8 cm are selected and cut back to one plant per pot. A small piece is cut from an infested leaf taken from the main colony and placed on each leaf of the test plants. This is done about 2 hours before treatment to allow the mites to move over to the test plant to lay eggs. The size of the cut, infested leaf is varied to obtain about 100 mites per leaf. At the time of test treatment, the piece of leaf used to transfer the mites is removed and discarded. The newly-infested plants are dipped in the test solution for 3 seconds with agitation and set in the hood to dry. After 2 days, one leaf is removed and mortality counts are made.

Aphis gossypii, Cotton Aphid (CA)

Cotton plants at the cotyledon stage are selected and cut back to one plant per pot. A heavily infested leaf is taken from the main colony and placed on top of each cotyledon. The aphids are allowed to transfer to the host plant overnight. At the time of test treatment, the leaf used to transfer the aphids is removed and discarded. The cotyledons are dipped in the test solution and allowed to dry. After 5 days, mortality counts are made.

Spodoptera eridania, Eggs-southern Armyworm and Diabrotica undecimpunctata howardi, Eggs-southern Corn Rootworm (SAW-Eggs) and (SCR-Eggs)

Wells containing artificial diet are treated with the test solutions and dried. The appropriate insect eggs are then placed in the wells. The wells are covered with vented, adhesive, clear plastic covers. After 7 days, mortality counts are made.

The tests are rated according to the scale shown below and the data obtained are shown in Table IV.

| Rating Scale | |
|---|---|
| 0 = no effect | 5 = 56–65% kill |
| 1 = 10–25% kill | 6 = 66–75% kill |
| 2 = 26–35% kill | 7 = 76–85% kill |
| 3 = 36–45% kill | 8 = 86–99% kill |
| 4 = 46–55% kill | 9 = 100% kill |

TABLE IV

Insecticidal and Acaricidal Evaluations of Test Compounds

| Ex. | CA (300$^1$) | SAW (300$^1$) | SAW Eggs (300$^1$) | SCR Eggs (1000$^1$) | TSM (300$^1$) | WCR (50$^1$) |
|---|---|---|---|---|---|---|
| 1 | | | 0 | 0 | | |
| 2 | | | 0 | 0 | | |
| 3 | | | 0 | 0 | | |
| 4 | 5 | 0 | 0 | 0 | 0 | 4 |
| 5 | 0 | 0 | 0 | 0 | 0 | 4 |
| 6 | 0 | 0 | 0 | | 0 | 7 |
| 7 | 0 | 0 | 0 | | 0 | 0 |
| 8 | 0 | 0 | 0 | | 0 | 0 |
| 9 | 0 | 0 | 0 | | 0 | 4 |
| 10 | 0 | 0 | 0 | | 0 | 0 |
| 11 | 0 | 0 | 0 | | 0 | 0 |
| 12 | 0 | 0 | 0 | | 0 | 0 |
| 13 | 7 | 0 | 0 | | 0 | 0 |
| 14 | 0 | 0 | 0 | | 0 | 0 |
| 15 | 0 | 0 | 0 | | 0 | 3 |
| 16 | 0 | 0 | 0 | | 0 | 0 |
| 17 | 0 | 0 | 0 | | 5 | 0 |
| 18 | 9 | 0 | 0 | 0 | 0 | 0 |
| 19 | 0 | 0 | 0 | 0 | 0 | 3 |
| 20 | 0 | 0 | 0 | 0 | 0 | 0 |
| 21 | 7 | 0 | 0 | 0 | 0 | 0 |
| 22 | 0 | 0 | 0 | 0 | 0 | 0 |
| 23 | 4 | 8 | 9 | 9 | 0 | 4 |
| 24 | 0 | 0 | 0 | 0 | 0 | 0 |
| 25 | 0 | 0 | 9 | 0 | 0 | 9 |
| 26 | 0 | 0 | 0 | 0 | 0 | 7 |
| 27 | 4 | 0 | 9 | 9 | 0 | 3 |
| 28 | 0 | 0 | 9 | 0 | 0 | 8 |
| 29 | 4 | 5 | 9 | 0 | 0 | 0 |
| 30 | 0 | 0 | 9 | 0 | 0 | 7 |
| 31 | 0 | 0 | | 0 | 0 | 0 |
| 32 | 0 | 0 | | 0 | 0 | 0 |
| 33 | 0 | 0 | | 0 | 0 | 2 |
| 34 | 0 | 5 | | 9 | 3 | 0 |
| 35 | 0 | 0 | | 9 | 3 | 0 |
| 36 | 0 | 1 | | 7 | 0 | 0 |
| 37 | 0 | 0 | | 0 | 0 | 0 |
| 38 | 0 | 0 | | 9 | 0 | 0 |
| 39 | 0 | 4 | | 0 | 0 | 8 |
| 40 | 0 | 3 | | 0 | 0 | 9 |
| 41 | 0 | 1 | | 0 | 0 | 9 |
| 42 | 0 | 0 | | 9 | 0 | 6 |
| 43 | 0 | 4 | | 9 | 0 | 7 |
| 44 | 0 | 5 | | 0 | 0 | 4 |
| 45 | 0 | 0 | | 7 | 0 | 8 |
| 46 | 0 | 1 | | 0 | 0 | 9 |
| 47 | 0 | 0 | 0 | 0 | 4 | 4 |
| 48 | 0 | 0 | 0 | 0 | 0 | 0 |
| 49 | 0 | 0 | 0 | 0 | 0 | 0 |
| 50 | 0 | 0 | 9 | 0 | 0 | 0 |
| 51 | 0 | 0 | 9 | 8 | 0 | 4 |
| 52 | 0 | 0 | 0 | 0 | 0 | 4 |
| 53 | 0 | 4 | 0 | 0 | 0 | 0 |
| 54 | 0 | 0 | 0 | 0 | 0 | 5 |
| 55 | 0 | 4 | 0 | 0 | 0 | 0 |
| 56 | 0 | 0 | 0 | 0 | 5 | 0 |
| 57 | 0 | 0 | 0 | 0 | 0 | 0 |
| 58 | 0 | 0 | 0 | 0 | 0 | 0 |
| 59 | 0 | 0 | 0 | 0 | 0 | 0 |
| 60 | 0 | 0 | 0 | 0 | 0 | 0 |

TABLE IV-continued

Insecticidal and Acaricidal Evaluations of Test Compounds

| Ex. | CA (300[1]) | SAW (300[1]) | SAW Eggs (300[1]) | SCR Eggs (1000[1]) | TSM (300[1]) | WCR (50[1]) |
|---|---|---|---|---|---|---|
| 61 | 5 | 0 | 0 | 0 | 0 | 0 |
| 62 | 5 | 0 | 0 | 0 | 0 | 0 |
| 63 | 0 | 0 | | | 0 | 0 |
| 64 | 0 | 0 | | | 9 | 0 |
| 65 | 0 | 0 | | | 0 | 9 |
| 66 | 0 | 0 | | | 0 | 8 |
| 67 | 0 | 0 | | | 0 | 9 |
| 68 | 0 | 0 | | | 0 | 3 |
| 69 | 0 | 0 | | | 0 | 0 |
| 70 | 0 | 0 | | | 0 | 0 |
| 71 | 0 | 0 | | | 0 | 0 |
| 72 | 0 | 0 | | | 0 | 0 |
| 73 | 0 | 0 | | | 0 | 0 |
| 74 | 0 | 0 | | | 0 | 0 |
| 75 | 0 | 0 | | | 0 | 0 |
| 76 | 0 | 0 | | | 0 | 0 |
| 77 | a | 0 | | | 3 | 0 |
| 78 | 0 | 0 | | | 0 | 0 |
| 88 | 0 | 0 | | 0 | 0 | 0 |
| 89 | 0 | 0 | | 0 | 0 | 0 |
| 90 | 0 | 0 | | 0 | 3 | 0 |
| 91 | 0 | 0 | | 0 | 0 | 0 |
| 92 | 0 | 0 | | 0 | 0 | 5 |
| 93 | 0 | 0 | | 0 | 0 | 0 |
| 94 | 0 | 0 | | 0 | 0 | 0 |
| 95 | 0 | 0 | | 0 | 0 | 4 |
| 96 | 0 | 0 | | 0 | 0 | 0 |
| 98 | 0 | 5 | 0 | 0 | 3 | 0 |
| 99 | 0 | 0 | 0 | 0 | 0 | 0 |
| 100 | 0 | 0 | 0 | 0 | 0 | 0 |
| 101 | 0 | 0 | 0 | 0 | 0 | 0 |
| 102 | 0 | 0 | 0 | 0 | 0 | 0 |
| 103 | 0 | 0 | 0 | 0 | 4 | 0 |
| 104 | 0 | 0 | 0 | 0 | 0 | 0 |
| 105 | 0 | 3 | 0 | 0 | 0 | 3 |
| 106 | 0 | 0 | 0 | 0 | 0 | 0 |
| 107 | 0 | 0 | 0 | 0 | 0 | 0 |
| 108 | 0 | 0 | 9 | 0 | 0 | 0 |
| 109 | 0 | 0 | 0 | 0 | 0 | 0 |
| 110 | 0 | 0 | 0 | 0 | 0 | 0 |
| 111 | 0 | 0 | 8 | 0 | 0 | 0 |
| 112 | 0 | 0 | 8 | 0 | 0 | 0 |
| 113 | 0 | 3 | 9 | 0 | 0 | 0 |
| 114 | 0 | 0 | 9 | 0 | 3 | 0 |
| 115 | 0 | 0 | 8 | 0 | 0 | 0 |
| 116 | 0 | 0 | 0 | 0 | 0 | 0 |
| 117 | 0 | 0 | 0 | 0 | 0 | 0 |
| 118 | 0 | 0 | 9 | 0 | 0 | 0 |
| 119 | 0 | 0 | 9 | 0 | 3 | 0 |
| 120 | 0 | 0 | 0 | 0 | 0 | 0 |
| 121 | 0 | 0 | 0 | 0 | 0 | 0 |
| 122 | 0 | 2 | 7 | 0 | 7 | 9 |
| 123 | 0 | 0 | 8 | 0 | 0 | 5 |
| 124 | 0 | 0 | 9 | 0 | 0 | 0 |
| 125 | 0 | 0 | 0 | 0 | 0 | 0 |
| 127 | 0 | 0 | 0 | 0 | 0 | 0 |
| 128 | 0 | 0 | 0 | 0 | 0 | 0 |
| 129 | 0 | 0 | 0 | 0 | 0 | 0 |
| 130 | 0 | 0 | 0 | 0 | 0 | 3 |
| 131 | 0 | 0 | 0 | 0 | 0 | 0 |
| 132 | 0 | 0 | 9 | 9 | 0 | 0 |
| 133 | 0 | 0 | 0 | 9 | 0 | 0 |
| 134 | 0 | 0 | 0 | 0 | 0 | 0 |
| 135 | 0 | 0 | 0 | 9 | 0 | 0 |
| 136 | 0 | 0 | 0 | 0 | 0 | 0 |
| 137 | 0 | 0 | 9 | 9 | 0 | 0 |
| 138 | 0 | 0 | 0 | 0 | 0 | 0 |
| 139 | 0 | 0 | 0 | 0 | 0 | 9 |
| 140 | 0 | 6 | 0 | 0 | 0 | 9 |
| 141 | 0 | 0 | 0 | 0 | 0 | 0 |
| 142 | 4 | 0 | 0 | 0 | 0 | 9 |
| 143 | 0 | 0 | 0 | 0 | 0 | 0 |
| 144 | 0 | 0 | 0 | 0 | 0 | 9 |
| 145 | 0 | 0 | 0 | 0 | 0 | 0 |
| 146 | 0 | 0 | 0 | 0 | 0 | 8 |
| 147 | 0 | 0 | 0 | 0 | 0 | 0 |
| 148 | 0 | 0 | 0 | 0 | 0 | 0 |
| 149 | 0 | 0 | 0 | 0 | 0 | 0 |
| 150 | 0 | 0 | | | 0 | 6 |
| 151 | 0 | 0 | | | 0 | 0 |
| 152 | 0 | 0 | | | 0 | 7 |
| 153 | 0 | 0 | | | 0 | 0 |
| 154 | 0 | 0 | | | 0 | 0 |
| 155 | 0 | 0 | | | 3 | 0 |
| 156 | 0 | 0 | | | 0 | 0 |
| 157 | 0 | 0 | | | 0 | 0 |
| 158 | 0 | 0 | 0 | 0 | 0 | 0 |
| 159 | 0 | 0 | | | 0 | 0 |
| 160 | 3 | 9 | | | 0 | 0 |
| 161 | 0 | 0 | | | 0 | 4 |
| 162 | 0 | 0 | | | 0 | 6 |
| 171 | 0 | 0 | 0 | 0 | 0 | 0 |
| 172 | 0 | 0 | 0 | 0 | 0 | 0 |
| 173 | 0 | 0 | 0 | 0 | 0 | 0 |
| 174 | 0 | 0 | 0 | 0 | 0 | 0 |
| 175 | 0 | 0 | 0 | 0 | 0 | 0 |
| 176 | 0 | 0 | 0 | 0 | 0 | 0 |
| 177 | 0 | 0 | 0 | 0 | 0 | 0 |
| 178 | 0 | 0 | 0 | 0 | 0 | 0 |
| 179 | 0 | 0 | 0 | 0 | 0 | 0 |
| 181 | 0 | 0 | 9 | 0 | 0 | 0 |
| 182 | 0 | 0 | 0 | 0 | 0 | 0 |
| 183 | 0 | 0 | 0 | 0 | 0 | 0 |
| 184 | 0 | 0 | 9 | 0 | 0 | 0 |
| 185 | 0 | 0 | 0 | 0 | 0 | 0 |
| 186 | 0 | 4 | 0 | 0 | 0 | 4 |
| 187 | 0 | 0 | 0 | 0 | 0 | 0 |
| 188 | 0 | 0 | 0 | 0 | 0 | 3 |
| 189 | 0 | 0 | 0 | 0 | 0 | 0 |
| 190 | 0 | 0 | 0 | 0 | 0 | 0 |
| 191 | 0 | 0 | 0 | 0 | 0 | 0 |
| 192 | 0 | 0 | 0 | 0 | 0 | 0 |
| 193 | 0 | 0 | 0 | 0 | 0 | 0 |
| 194 | 0 | 0 | 0 | 0 | 0 | 0 |
| 195 | 0 | 0 | 0 | 0 | 0 | 0 |
| 196 | 0 | 0 | 0 | 0 | 0 | 9 |
| 197 | 5 | 0 | 9 | 0 | 0 | 0 |
| 198 | 0 | 0 | 9 | 0 | 0 | 7 |
| 199 | 0 | 0 | 9 | 0 | 0 | 8 |
| 200 | 0 | 0 | 9 | 0 | 0 | 4 |
| 201 | 0 | 0 | 0 | 0 | 0 | 7 |
| 202 | 0 | 0 | 9 | 0 | 0 | 9 |
| 203 | 0 | 0 | 9 | 9 | 0 | 8 |

[1]rates in ppm

What is claimed is:

1. A method for the control of helminth, nematode, insect or acarid pests or parasites which comprises contacting aid pests or parasites or their food supply, habitat or breeding grounds with a pesticidally or parasiticidally effective amount of a compound having the structural formula I

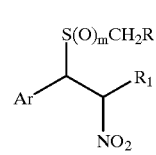

(I)

wherein
Ar is phenyl optionally substituted with any combination of one to five halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups, one to three $C_1$–$C_4$haloalkylthio groups, one benzylthio group or one $SCH_2CO_2R_2$ group or 1- or 2-naphthyl optionally substituted with any combination of one to five halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups;

R is hydrogen, $CO_2R_3$, $C(O)NR_4R_5$, $(CH_2)_nCR_2(NR_4R_5)$ $CO_2R_3$, $CH(OR_6)CH_2OR_7$, $CH(CH_2OR_8)SCH(R_9)$ $CH_2NO_2$, $C_1$–$C_4$alkyl, $C_1$–$C_4$haloalkyl, $C_2$–$C_4$alkenyl, $C_2$–$C_4$haloalkenyl, phenyl optionally substituted with any combination of one to five halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups, 2- or 3-furyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups, or 2- or 3-thienyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups;

$R_2$, $R_6$, $R_7$ and $R_8$ are each independently hydrogen or $C_1$–$C_6$alkyl;

m is 0, 1 or 2;

n is 0 or 1;

$R_9$ is phenyl optionally substituted with any combination of one to five halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups;

$R_3$ is hydrogen, $C_1$–$C_{10}$alkyl, $CH_2(C_1$–$C_{10}$haloalkyl), $C_3$–$C_{10}$alkenyl, $C_3$–$C_{10}$haloalkenyl, a cation, benzyl optionally substituted on the ring with any combination of one to five halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups, or phenyl optionally substituted with any combination of one to five halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups;

$R_4$ and $R_5$ are each independently hydrogen, $C_1$–$C_{10}$alkyl, $CH_2(C_1$–$C_{10}$haloalkyl), $C_3$–$C_{10}$alkenyl, $C_3$–$C_{10}$haloalkenyl, benzyl optionally substituted on the ring with any combination of one to five halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups, or phenyl optionally substituted with any combination of one to five halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups, and when $R_4$ and $R_5$ are taken together with the atom to which they are attached, they may form a five- or six-membered ring wherein $R_4R_5$ is represented by: —$(CH_2)_4$—, —$(CH_2)_5$— or —$(CH_2)_2O(CH_2)_2$—; and $R_1$ is hydrogen, $C_1$–$C_4$alkyl or phenyl optionally substituted with any combination of one to five halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups.

2. The method according to claim 1, wherein the compound is selected from the group consisting of
methyl{[alpha-(nitromethyl)benzyl]thio}acetate;
{[alpha-(nitromethyl)benzyl]thio}acetic acid;
ethyl{[p-methyl-alpha-(nitromethyl)benzyl]thio}acetate;
butyl{[alpha-(nitromethyl)benzyl]thio}acetate;
methyl{[3,4-(methylenedioxy)-alpha-(nitromethyl)benzyl]thio}acetate;
ethyl{[3,4-(methylenedioxy)-alpha-(nitromethyl)benzyl]thio}acetate;
butyl{[3,4-(methylenedioxy)-alpha-(nitromethyl)benzyl]thio}acetate;
methyl{[p-methyl-alpha-(nitromethyl)benzyl]thio}acetate;
butyl{[p-methyl-alpha-(nitromethyl)benzyl]thio}acetate;
methyl{[o-fluoro-alpha-(nitromethyl)benzyl]thio}acetate;
ethyl{[o-fluoro-alpha-(nitromethyl)benzyl]thio}acetate;
butyl{[o-fluoro-alpha-(nitromethyl)benzyl]thio}acetate;
methyl{[p-methoxy-alpha-(nitromethyl)benzyl]thio}acetate;
ethyl{[p-methoxy-alpha-(nitromethyl)benzyl]thio}acetate;
butyl{[p-methoxy-alpha-(nitromethyl)benzyl]thio}acetate;
p-[1-(allylthio)-2-nitroethyl]anisole;
methyl{[m-methoxy-alpha-(nitromethyl)benzyl]thio}acetate;
ethyl{[m-methoxy-alpha-(nitromethyl)benzyl]thio}acetate;
{[p-fluoro-alpha-(nitromethyl)benzyl]thio}acetic acid;
{[3,4-(methylenedioxy)-alpha-(nitromethyl)benzyl]thio}acetic acid;
{[2-nitro-1-(p-tolyl)ethyl]thio}acetic acid;
{[p-isopropyl-alpha-(nitromethyl)benzyl]thio}acetic acid;

{[o-fluoro-alpha-(nitromethyl)benzyl]thio}acetic acid;
{[m-methoxy-alpha-(nitromethyl)benzyl]thio}acetic acid;
{[p-methoxy-alpha-(nitromethyl)benzyl]thio}acetic acid;
{[p-chloro-alpha-(nitromethyl)benzyl]thio}acetic acid;
2,3-bis{[alpha-(nitromethyl)benzyl]thio}-1-propanol; and
3-{[alpha-(nitromethyl)benzyl]thio}alanine.

3. The method according to claim 1, wherein the compound is selected from the group consisting of
methyl{[alpha-(nitromethyl)benzyl]thio}acetate;
{[alpha-(nitromethyl)benzyl]thio}acetic acid;
ethyl{[p-methyl-alpha-(nitromethyl)benzyl]thio}acetate;
ethyl{[3,4-(methylenedioxy)-alpha-(nitromethyl)benzyl] thio}acetate;
methyl{[p-methyl-alpha-(nitromethyl)benzyl]thio}acetate;
ethyl{[p-methoxy-alpha-(nitromethyl)benzyl]thio}lacetate;
{[p-fluoro-alpha-(nitromethyl)benzyl]thio}acetic acid;
{[3,4-(methylenedioxy)-alpha-(nitromethyl)benzyl] thio}acetic acid;
{[2-nitro-1-(p-tolyl)ethyl]thio}acetic acid;
{[p-isopropyl-alpha-(nitromethyl)benzyl]thio}acetic acid;
{[o-fluoro-alpha-(nitromethyl)benzyl]thio}acetic acid;
{[m-methoxy-alpha-(nitromethyl)benzyl]thio}acetic acid;
{[p-methoxy-alpha-(nitromethyl)benzyl]thio}acetic acid;
2,3-bis{[alpha-(nitromethyl)benzyl]thio}-1-propanol; and
3-{[alpha-(nitromethyl)benzyl]thio}alanine.

4. The method according to claim 1, wherein the pest is a nematode.

5. A method for the protection of growing plants from attack or infestation by nematode, insect or acarid pests which comprises applying to the foliage of the plants, or to the soil or water in which they are growing, a pesticidally effective amount of a compound having the structural formula I

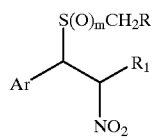

(Ia)

wherein Ar, m, R and $R_1$ are as described in claim 1.

6. The method according to claim 5, wherein the compound is selected from the group consisting of
methyl{[alpha-(nitromethyl)benzyl]thio}acetate;
{[alpha-(nitromethyl)benzyl]thio}acetic acid;
ethyl{[p-methyl-alpha-(nitromethyl)benzyl]thio}acetate;
butyl{[alpha-(nitromethyl)benzyl]thio}acetate;
methyl{[3,4-(methylenedioxy)-alpha-(nitromethyl)benzyl] thio}acetate;
ethyl{[3,4-(methylenedioxy)-alpha-(nitromethyl)benzyl] thio}acetate;
butyl{[3,4-(methylenedioxy)-alpha-(nitromethyl)benzyl] thio}acetate;
methyl{[p-methyl-alpha-(nitromethyl)benzyl]thio}acetate;
butyl{[p-methyl-alpha-(nitromethyl)benzyl]thio}acetate;
methyl{[o-fluoro-alpha-(nitromethyl)benzyl]thio}acetate;
ethyl{[o-fluoro-alpha-(nitromethyl)benzyl]thio}acetate;
butyl{[o-fluoro-alpha-(nitromethyl)benzyl]thio}acetate;
methyl{[p-methoxy-alpha-(nitromethyl)benzyl] thio}acetate;
ethyl{[p-methoxy-alpha-(nitromethyl)benzyl]thio}acetate;
butyl{[p-methoxy-alpha-(nitromethyl)benzyl]thio}acetate;
p-[1-(allylthio)-2-nitroethyl]anisole;
methyl{[m-methoxy-alpha-(nitromethyl)benzyl] thio}acetate;
ethyl{[m-methoxy-alpha-(nitromethyl)benzyl]thio}acetate;
{[p-fluoro-alpha-(nitromethyl)benzyl]thio}acetic acid;
{[3,4-(methylenedioxy)-alpha-(nitromethyl)benzyl] thio}acetic acid;
{[2-nitro-1-(p-tolyl)ethyl]thio}acetic acid;
{[p-isopropyl-alpha-(nitromethyl)benzyl]thio}acetic acid;
{[o-fluoro-alpha-(nitromethyl)benzyl]thio}acetic acid;
{[m-methoxy-alpha-(nitromethyl)benzyl]thio}acetic acid;
{[p-methoxy-alpha-(nitromethyl)benzyl]thio}acetic acid;
{[p-chloro-alpha-(nitromethyl)benzyl]thio}acetic acid;
2,3-bis{[alpha-(nitromethyl)benzyl]thio}-1-propanol; and
3-{[alpha-(nitromethyl)benzyl]thio}alanine.

7. The method according to claim 5, wherein the compound is selected from the group consisting of
methyl{[alpha-(nitromethyl)benzyl]thio}acetate;
{[alpha-(nitromethyl)benzyl]thio}acetic acid;
ethyl{[p-methyl-alpha-(nitromethyl)benzyl]thio}acetate;
ethyl{[3,4-(methylenedioxy)-alpha-(nitromethyl)benzyl] thio}acetate;
methyl{[p-methyl-alpha-(nitromethyl)benzyl]thio}acetate;
ethyl{[p-methoxy-alpha-(nitromethyl)benzyl]thio}acetate;
{[p-fluoro-alpha-(nitromethyl)benzyl]thio}acetic acid;
{[3,4-(methylenedioxy)-alpha-(nitromethyl)benzyl] thio}acetic acid;
{[2-nitro-1-(p-tolyl)ethyl]thio}acetic acid;
{[p-isopropyl-alpha-(nitromethyl)benzyl]thio}acetic acid;
{[o-fluoro-alpha-(nitromethyl)benzyl]thio}acetic acid;
{[m-methoxy-alpha-(nitromethyl)benzyl]thio}acetic acid;
{[p-methoxy-alpha-(nitromethyl)benzyl]thio}acetic acid;
2,3-bis{[alpha-(nitromethyl)benzyl]thio}-1-propanol; and
3-{[alpha-(nitromethyl)benzyl]thio}alanine.

8. The method according to claim 5, wherein the pest is a nematode.

9. A method for treating, controlling, preventing or protecting a warm-blooded animal or a fish against infestation or infection by helminths which comprises orally, topically or parenterally administering or applying to said animal or fish an anthelmintically effective amount of a compound having the structural formula I

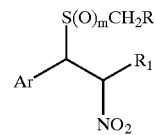

(I)

wherein Ar, m, R and $R_1$ are as described in claim 1.

10. A compound having the structural formula Ia

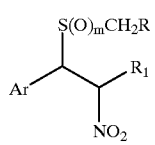

(Ia)

wherein
Ar is phenyl optionally substituted with any combination of one to five halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups, one to three $C_1$–$C_4$haloalkylthio groups, one benzylthio group or one $SCH_2CO_2R_2$ group or
1- or 2-naphthyl optionally substituted with any combination of one to five halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups;

R is hydrogen, $CO_2R_3$, $C(O)NR_4R_5$, $(CH_2)_nCR_2(NR_4R_5)CO_2R_3$, $CH(OR_6)CH_2OR_7$, $CH(CH_2OR_8)SCH(R_9)CH_2NO_2$, $C_1$–$C_4$alkyl, $C_1$–$C_4$haloalkyl, $C_2$–$C_4$alkenyl, $C_2$–$C_4$haloalkenyl, phenyl optionally substituted with any combination of one to five halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups, 2- or 3-furyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups, or 2- or 3-thienyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups;

$R_2$, $R_6$, $R_7$ and $R_8$ are each independently hydrogen or $C_1$–$C_6$alkyl;

m is 0, 1 or 2;

n is 0 or 1;

$R_9$ is phenyl optionally substituted with any combination of one to five halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups;

$R_3$ is hydrogen, $C_1$–$C_{10}$alkyl, $CH_2(C_1$–$C_{10}$haloalkyl), $C_3$–$C_{10}$alkenyl, $C_3$–$C_{10}$haloalkenyl, a cation, benzyl optionally substituted on the ring with any combination of one to five halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups, or phenyl optionally substituted with any combination of one to five halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups;

$R_4$ and $R_5$ are each independently hydrogen, $C_1$–$C_{10}$alkyl, $CH_2(C_1$–$C_{10}$haloalkyl), $C_3$–$C_{10}$alkenyl, $C_3$–$C_{10}$haloalkenyl, benzyl optionally substituted on the ring with any combination of one to five halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups, or phenyl optionally substituted with any combination of one to five halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups, and when $R_4$ and $R_5$ are taken together with the atom to which they are attached, they may form a five- or six-membered ring wherein $R_4R_5$ is represented by: —$(CH_2)_4$—, —$(CH_2)_5$— or —$(CH_2)_2O(CH_2)_2$—; and $R_1$ is hydrogen, $C_1$–$C_4$alkyl or phenyl optionally substituted with any combination of one to five halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one to three $C_1$–$C_4$alkylthio groups or one to three $C_1$–$C_4$haloalkylthio groups; and provided that Ar is other than phenyl optionally substituted with any combination of one to three halogen atoms, one or two nitro groups, one or two cyano groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups when R is: (1) $CO_2R_3$ and $R_3$ is hydrogen or $C_1$–$C_{10}$alkyl, (2) $(CH_2)_nCR_2(NR_4R_5)CO_2R_3$, n is 0 and $R_2$, $R_3$, $R_4$ and $R_5$ are hydrogen, (3) $C_1$–$C_4$ alkyl, (4) $C_2$–$C_4$ alkenyl or (5) phenyl optionally substituted with one to five halogen atoms.

11. The compound according to claim 10, wherein the compound is selected from the group consisting of
methyl{[3,4-(methylenedioxy)-alpha-(nitromethyl)benzyl]thio}acetate;
ethyl{[3,4-(methylenedioxy)-alpha-(nitromethyl)benzyl]thio}acetate;
butyl{[3,4-(methylenedioxy)-alpha-(nitromethyl)benzyl]thio}acetate;
{[3,4-(methylenedioxy)-alpha-(nitromethyl)benzyl]thio}acetic acid;
2,3-bis{[alpha-(nitromethyl)benzyl]thio}-1-propanol; and
3-{[alpha-(nitromethyl)benzyl]thio}alanine.

12. The compound according to claim 10, wherein the compound is selected from the group consisting of
ethyl{[3,4-(methylenedioxy)-alpha-(nitromethyl)benzyl]thio}acetate;
{[3,4-(methylenedioxy)-alpha-(nitromethyl)benzyl]thio}acetic acid;
2,3-bis{[alpha-(nitromethyl)benzyl]thio}-1-propanol; and
3-{[alpha-(nitromethyl)benzyl]thio}alanine.

13. A composition for the control of helminth, nematode, insect or acarid pests or parasites which comprises an agronomically or pharmaceutically acceptable carrier and a pesticidally or parasiticidally effective amount of a compound having the structural formula I

(I)

wherein Ar, m, R and R₁ are as described in claim 10.

14. The composition according to claim 13, wherein the compound is selected from the group consisting of
methyl{[alpha-(nitromethyl)benzyl]thio}acetate;
{[alpha-(nitromethyl)benzyl]thio}acetic acid;
ethyl{[p-methyl-alpha-(nitromethyl)benzyl]thio}acetate;
butyl{[alpha-(nitromethyl)benzyl]thio}acetate;
methyl{[3,4-(methylenedioxy)-alpha-(nitromethyl)benzyl] thio}acetate;
ethyl{[3,4-(methylenedioxy)-alpha-(nitromethyl)benzyl] thio}acetate;
butyl{[3,4-(methylenedioxy)-alpha-(nitromethyl)benzyl] thio}acetate;
methyl{[p-methyl-alpha-(nitromethyl)benzyl]thio}acetate;
butyl{[p-methyl-alpha-(nitromethyl)benzyl]thio}acetate;
methyl{[o-fluoro-alpha-(nitromethyl)benzyl]thio}acetate;
ethyl{[o-fluoro-alpha-(nitromethyl)benzyl]thio}acetate;
butyl{[o-fluoro-alpha-(nitromethyl)benzyl]thio}acetate;
methyl{[p-methoxy-alpha-(nitromethyl)benzyl] thio}acetate;
ethyl{[p-methoxy-alpha-(nitromethyl)benzyl]thio}acetate;
butyl{[p-methoxy-alpha-(nitromethyl)benzyl]thio}acetate;
p-[1-(allylthio)-2-nitroethyl]anisole;
methyl{[m-methoxy-alpha-(nitromethyl)benzyl] thio}acetate;
ethyl{[m-methoxy-alpha-(nitromethyl)benzyl]thio}acetate;
{[p-fluoro-alpha-(nitromethyl)benzyl]thio}acetic acid;
{[3,4-(methylenedioxy)-alpha-(nitromethyl)benzyl] thio}acetic acid;
{[2-nitro-1-(p-tolyl)ethyl]thio}acetic acid;
{[p-isopropyl-alpha-(nitromethyl)benzyl]thio}acetic acid;
{[o-fluoro-alpha-(nitromethyl)benzyl]thio}acetic acid;
{[m-methoxy-alpha-(nitromethyl)benzyl]thio}acetic acid;
{[p-methoxy-alpha-(nitromethyl)benzyl]thio}acetic acid;
{[p-chloro-alpha-(nitromethyl)benzyl]thio}acetic acid;
2,3-bis{[alpha-(nitromethyl)benzyl]thio}-1-propanol; and
3-{[alpha-(nitromethyl)benzyl]thio}alanine.

15. The composition according to claim 13, wherein the compound is selected from the group consisting of
methyl{[alpha-(nitromethyl)benzyl]thio}acetate;
{[alpha-(nitromethyl)benzyl]thio}acetic acid;
ethyl{[p-methyl-alpha-(nitromethyl)benzyl]thio}acetate;
ethyl{[3,4-(methylenedioxy)-alpha-(nitromethyl)benzyl] thio}acetate;
methyl{[p-methyl-alpha-(nitromethyl)benzyl]thio}acetate;
ethyl{[p-methoxy-alpha-(nitromethyl)benzyl]thio}acetate;
{[p-fluoro-alpha-(nitromethyl)benzyl]lacetic acid;
{[3,4-(methylenedioxy)-alpha-(nitromethyl)benzyl] thio}acetic acid;
{[2-nitro-1-(p-tolyl)ethyl]thio}acetic acid;
{[p-isopropyl-alpha-(nitromethyl)benzyl]thio}acetic acid;
{[o-fluoro-alpha-(nitromethyl)benzyl]thio}acetic acid;
{[m-methoxy-alpha-(nitromethyl)benzyl]thio}acetic acid;
{[p-methoxy-alpha-(nitromethyl)benzyl]thio}acetic acid;
2,3-bis{[alpha-(nitromethyl)benzyl]thio}-1-propanol; and
3-{[alpha-(nitromethyl)benzyl]thio}alanine.

* * * * *